United States Patent [19]

Bonjouklian et al.

[11] Patent Number: 5,378,725
[45] Date of Patent: Jan. 3, 1995

[54] INHIBITION OF PHOSPHATIDYLINOSITOL 3-KINASE WITH WORTMANNIN AND ANALOGS THEREOF

[75] Inventors: Rosanne Bonjouklian, Zionsville; Chris J. Vlahos, Carmel, both of Ind.; Garth Powis, Tucson, Ariz.

[73] Assignees: The Arizona Board of Regents, Tucson, Ariz.; Eli Lilly and Company, Indianapolis, Ind.

[21] Appl. No.: 94,279

[22] Filed: Jul. 19, 1993

[51] Int. Cl.$^6$ .................. A61K 31/35; A61K 31/34
[52] U.S. Cl. ...................... 514/453; 514/468
[58] Field of Search ..................... 514/453, 468

[56] References Cited

U.S. PATENT DOCUMENTS 3,668,222  6/1972  Hauser ................. 260/343.2 R
4,988,682  1/1991  Kozikowski ............. 514/150

FOREIGN PATENT DOCUMENTS 028948  12/1991  Japan .

OTHER PUBLICATIONS

Matter, W. F., et al., *Biochem. Biophys. Res. Commun.* 186(2):624–631 (1992).
Haeflinger, W., et al., *Helv. Chem. Acta*, 56(8):2901–2904 (1973).
MacMillan, J., et al., *J. Chem. Soc.* Perkin I, 2892–2898 (1972).
Abbas, H. K., et al., *Appl. Environ. Microbiol.* 54(5):1268–1274 (1988).
Shibasaki, F., et al., *J. Biol. Chem.*, 266(13):8108–8114 (1991).
Nakanishi, S., et al., *J. Biol. Chem.*, 267(4):2157–2163 (1992).
Ohara–Imaizumi, M., et al., *Biochem. Biophys. Res. Commun.*, 185(3):1016–1021 (1992).
Kaplan, D. R., et al., *Cell*, 50:1027–1029 (1987).
Valius, M., et al., Cell, 73:321–334 (1993).
Coughlin, S. R., et al., *Science*, 243:1191–1194 (1989).
Baggiolini, M., et al., *Exp. Cell Res.*, 169:408–418 (1987).
Kimura, K., et al., *Ninth Annual Meeting on Oncogenes*, Abstract:203 (1993).

*Primary Examiner*—Raymond J. Henley, III
*Attorney, Agent, or Firm*—Steven A. Fontana; David E. Boone

[57] ABSTRACT

Wortmannin and certain of its analogs are inhibitors of phosphatidylinositol 3-kinase. The compounds are particularly useful for inhibiting phosphatidylinositol 3-kinase in mammals and for treating phosphatidylinositol 3-kinase-dependent conditions, especially neoplasms, in mammals.

9 Claims, No Drawings

INHIBITION OF PHOSPHATIDYLINOSITOL 3-KINASE WITH WORTMANNIN AND ANALOGS THEREOF

This invention was made with government support under UO1 CA 52995 awarded by the National Institutes of Health. The government has certain rights in this invention.

TECHNICAL FIELD OF THE INVENTION

The present invention relates to a method of inhibiting phosphatidylinositol 3-kinase (PI 3-kinase) in a lysed or whole cell by contacting the lysed or whole cell with a compound known as wortmannin or one of certain wortmannin analogs. Such compounds also can be used to selectively inhibit phosphatidylinositol 3-kinase in mammals, particularly humans, and to treat phosphatidylinositol 3-kinase-dependent conditions, particularly neoplasms, in humans.

BACKGROUND OF THE INVENTION

The metabolism of inositolphospholipids is believed to be an essential part of the receptor-mediated signal transduction pathways in response to various hormones and growth factors [see, e.g., Berridge, M. J., et al., *Nature*, 312:315-321 (1984); Nishizuka, Y., *Science*, 225: 1365-1370 (1984)].

In this signaling pathway, two intracellular second messengers, inositol 1,4,5-trisphosphate and diacylglycerol are generated through the hydrolysis of phosphatidyl 4,5-bisphosphate by phospholipase C. Inositol 1,4,5-trisphosphate releases $Ca^{2+}$ from intracellular $Ca^{2+}$ stores leading to the activation of $Ca^{2+}$/calmodulin-dependent kinase; diacylglycerol activates protein kinase C. Following breakdown, phosphatidylinositol 4,5-bisphosphate is rapidly resynthesized by stepwise phosphorylation of phosphatidylinositol by phosphatidylinositol 4-kinase and phosphatidylinositol-4-phosphate kinase. These 2 kinases appear to play important roles in the production of second messengers (see, e.g., Duell, T. F., U.S. Pat. No. 5,001,064 (1991); Shibasaki, F., et al., *J. Biol. Chem.*, 266 (13): 8108-8114 (1991).

More recently, the existence of another phosphatidylinositol kinase has been identified and associated with certain activated tyrosine kinases [Courtneidge, S. A., et al., *Cell*, 50:1031-1037 (1987); Kaplan, D. R., et al., *Cell*, 50: 1021-1029 (1987)]. This kinase, identified as phosphatidylinositol 3-kinase has been found to phosphorylate the 3-position of the inositol ring of phosphatidylinositol (PI) to form phosphatidylinositol 3-phosphate (PI-3P) [Whitman, D., et al., *Nature*, 332:664-646 (1988).

In addition to PI, this enzyme also can phosphorylate phosphatidylinositol 4-phosphate and phosphatidylinositol 4,5-bisphosphate to produce phosphatidylinositol 3,4-bisphosphate and phosphatidylinositol 3,4,5-trisphosphate (PIP3), respectively [Auger, K. R., et al., *Cell*, 57:167-175 (1989)].

PI 3-kinase physically associates with tyrosine kinases such as pp60$^{v\text{-}src}$, polyoma middle T/pp60$^{c\text{-}src}$, platelet-derived growth factor receptor, colony stimulation factor-1 receptor, and insulin receptor (see, e.g., Shibasaki supra), suggesting it has important, but yet undefined roles in signal transduction, mitogenesis, cell transformation, and other cellular events involving protein tyrosine kinases that associate with and activate PI 3-kinase. PI 3-kinase activity also has been identified in association with G-protein receptors in neutrophils and platelets in neutrophils [Traynor-Kaplan, A. E., et al., *Nature*, 334:353-356 (1988); and Mitchell, C. A., et al., *Proc. Nat. Acad. Sci.*, 87:9396-9400 (1990)]. However, activation of PI 3-kinase in the neutrophil occurs independently of tyrosine phosphorylation [Vlahos, C. J., et al., FEBS Letters, 309(3):242-248 (1992)].

PI 3-kinase exists as a tightly associated heterodimer of an 85 kDa regulatory subunit and an 110 kDa catalytic subunit, and is found in cellular complexes with almost all ligand-activated growth factor receptors and oncogene protein tyrosine kinases [Cantley, L. C., et *Cell*, 64:281-302 (1991)]. The 85 kDa regulatory subunit apparently acts as an adaptor protein which allows the 110 kDa catalytic subunit of PI 3-kinase to interact with growth factor receptors and tyrosine phosphorylated proteins [Margolis, C., *Cell Growth Differ.*, 3:73-80 (1992)].

Although PI 3-kinase appears to be an important enzyme in signal transduction, with particular implications relative to mitogenesis and the malignant transformation of cells, only a limited number of compounds have been identified as having inhibitory activity against PI 3-kinase [see, e.g., Matter, W. F., et al., *Biochem. Biophys, Res. Commun.*, 186: 624-631 (1992)]. Contrary to the selective PI 3-kinase activity of the compounds used in the methods of the present invention, the bioflavinoid compounds used by Matter, et al., particularly quercetin and certain analogs thereof, inhibit PI 3-kinase and other kinases such as protein kinase C and PI 4-kinase (Matter, et al., supra).

Thus, the present invention provides a method for inhibiting phosphatidylinositol 3-kinase in a lysed or whole cell with wortmannin or one of certain wortmannin analogs.

The present invention also provides a method for inhibiting phosphatidylinositol 3-kinase in mammals, particularly humans, using wortmannin or one of certain analogs thereof.

Furthermore, the present invention provides a method for treating phosphatidylinositol 3-kinase-dependent conditions, particularly neoplasms, in mammals.

SUMMARY OF THE INVENTION

The present invention provides a method for inhibiting phosphatidylinositol 3-kinase in a lysed or whole cell comprising contacting a lysed or whole cell with a compound selected from the group consisting of

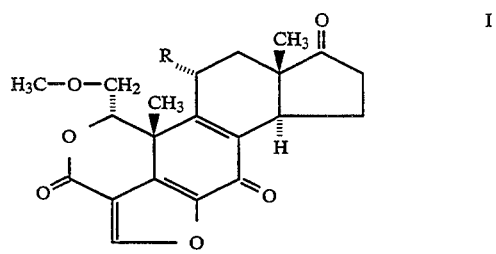

wherein R is H or acetoxy;

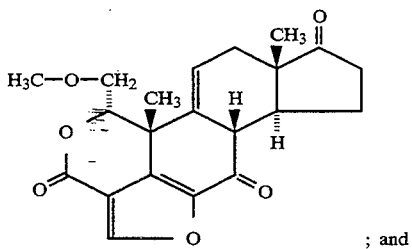

II

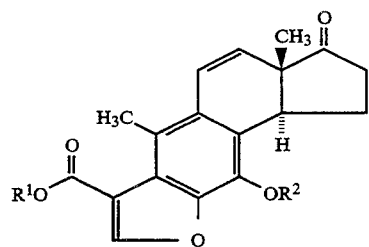

III wherein
R[1] is H, methyl, or ethyl; and
R[2] is H or CH$_3$.

The present invention also provides a method for inhibiting phosphatidylinositol 3-kinase in a mammal comprising administering to said mammal a phosphatidylinositol 3-kinase inhibiting amount of a compound selected from the group consisting of compounds of formulae I, II, and III above.

The present invention further provides a method for treating a phosphatidylinositol 3-kinase-dependent condition in a mammal in need of such treatment comprising administering to said mammal a phosphatidylinositol 3-kinase inhibiting amount of a compound selected from the group consisting of compounds of formulae I, II, and III above.

DETAILED DESCRIPTION OF THE INVENTION

As mentioned above, the present invention relates to a method for inhibiting phosphatidylinositol 3-kinase in a lysed or whole cell comprising contacting said lysed or whole cell with a compound selected from the group consisting of

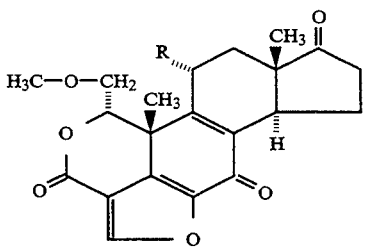

I wherein R is H or acetoxy;

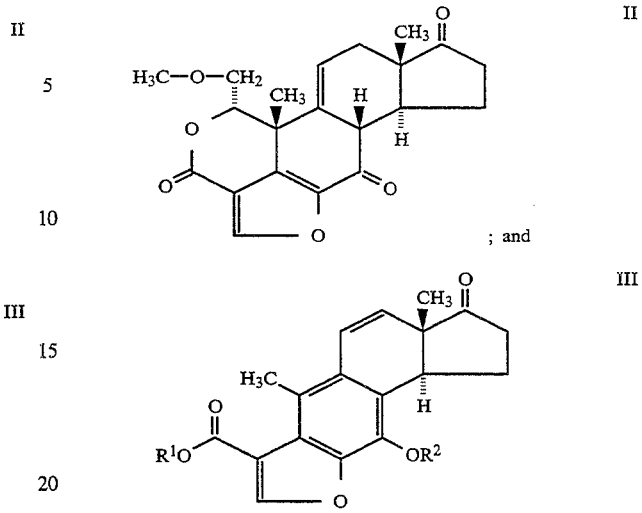

wherein
R[1] is H, methyl, or ethyl; and
R[2] is H or CH$_3$.

The compounds of formulae I, II, and III are known in the art. Table 1 below shows the trivial names of the preferred compounds used in the methods of the present invention.

TABLE 1

Wortmannin and Preferred Wortmannin Analogs

| Formula Designation | R | R[1] | R[2] | Trivial Name |
|---|---|---|---|---|
| Ia | acetoxy | NA | NA | wortmannin |
| Ib | H | NA | NA | 11-desacetoxywortmannin |
| II | NA | NA | NA | Δ9,11-dehydro-desacetoxywortmannin |
| IIIa | NA | H | H | opened A-ring acid of wortmannin |
| IIIb | NA | methyl | H | opened A-ring methyl ester of wortmannin |

The biosynthetic production of wortmannin (Ia) is well known in the art. Typically, it is produced by the fermentation of any one of a number of previously disclosed microorganisms such as *Talaromyces wortmannin* [Nakanishi, et al., *J. Biol. Chem.*, 267 (4): 2157–2163 (1992)]; and *Penicillium wortmannii, Myrothecium roridium*, and *Fusarium oxysporum* [Abbas, et al., *Appl. Environ. Microbiol.*, 54(5): 1267–1274 (1988)]. Following fermentation, wortmannin is extracted and purified via known methods.

Preferably, wortmannin is microbially synthesized and isolated in substantially pure form from a fermentation culture identified as A24603.1.

Culture A24603.1 will be deposited in compliance with Budapest Treaty, and made part of the stock culture collection of the Midwest Area Northern Regional Research Center, Agricultural Research Service, United States Department of Agriculture, 1815 North University Street, Peoria, Ill., 61604.

The permanency of the deposit of this culture at the Midwest Area Northern Regional Research Center at Peoria, Illinois, and ready accessibility thereto by the public will be afforded throughout the effective life of the patent in the event the patent is granted. Access to the culture will be available during pendency of the application under 37 C.F.R. §1.14 and 35 U.S.C. §112.

All restrictions on the availability to the public of the culture will be irrevocably removed upon granting of the patent.

Wortmannin is produced by culturing the above-referenced A24603 1 strain under submerged aerobic conditions in a suitable culture medium until a recoverable amount of wortmannin is produced. Wortmannin can be recovered using various isolation and purification procedures understood in the art.

The medium used to grow the A24603.1 culture can be any one of a number of media. For economy in production, optimal yield, and ease of product isolation, however, preferred carbon sources in large-scale fermentation are glucose and soluble starch such as corn starch. Maltose, ribose, xylose, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolized casein, beef extract, and the like can also be used.

Among the nutrient inorganic salts which can be incorporated in the culture media are the customary soluble salts capable of yielding calcium, magnesium, sodium, ammonium, chloride, carbonate, sulfate, nitrate, zinc, and like ions.

Essential trace elements necessary for the growth and development of the organism also should be included in the culture medium. Such trace elements commonly occur as impurities in other substituents of the medium in amounts sufficient to meet the growth requirements on the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Wortmannin is produced by the A24603.1 organism when grown at temperatures between about 23° and 29° C. Optimum temperature for wortmannin production appears to be about 25° C.

As is customary in submerged aerobic culture processes, sterile air is blown into the vessels from the bottom while the medium is stirred with conventional turbine impellors. In general, the aeration rate and agitation rate should be sufficient to maintain a level of dissolved oxygen of at least 45% of air saturation with an internal vessel pressure of about 5 atmospheres.

Production of wortmannin can be observed during the fermentation by testing PI 3-kinase extracts from the broth. A PI 3-kinase assay system described infra is a useful assay for this purpose.

Following its production, wortmannin can be recovered from the fermentation medium by methods used in the art. The wortmannin produced during fermentation of the A24603.1 organism occurs mainly in the broth.

Typically, wortmannin can be recovered from the biomass by a variety of techniques. A preferred technique involves filtering whole fermentation broth with a ceramic filter. The filtrate is eluted with an organic solvent such as ethylacetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

11-deacetoxywortmannin (formula Ib) also is known in the art as are methods for its preparation. Generally, this compound can be biosynthetically produced by fermenting a culture of Penicillium funiculosum Thom [see, e.g., Baggolini, et al., Exp. Cell Res., 169:408–418 (1987)]; but, preferably, is chemically derived from wortmannin by the method disclosed by Haeflinger, et al., Helv. Chem. Acta, 56(8): 2901–2904 (1973).

Similarly, the preparation of Δ9,11-dehydrodesacetoxywortmannin (formula II) is known in the art and is described by Haeflinger, et al., supra; and the preparation of compounds of formula III is described by MacMillan, J., et al., J. Chem. Soc, Perkin I: 2892–2898 (1972).

In the present method, compounds of formulae I, II, and III are effective for selectively inhibiting phosphatidylinositol 3-kinase in a lysed or whole cell. This method can be carried out in vitro or in vivo and can be utilized as a pharmacological tool for studying, for example, the involvement of PI 3-kinase in mitogenesis, cellular proliferation, or cellular differentiation. The compounds of formulae I, II, and III also can be radiolabeled (e.g., tritiated), to provide for easier detection of such compounds in cells.

When compounds of formulae I, II, or III are used for this method, such a compound is dissolved in an organic solvent such as dimethylsulfoxide (DMSO), and diluted with HEPES buffer (pH 7.5, containing 15 mM of $MgCl_2$ and 1 mM of EGTA), to the desired concentration. The resulting preparation is then placed in contact with purified PI 3-kinase or a cell according to methods well known in the art.

Another embodiment of the present invention provides a method for inhibiting phosphatidylinositol 3-kinase in a mammal, particularly humans, comprising administering to said mammals a phosphatidylinositol 3-kinase inhibiting amount of a compound selected from the group consisting of compounds of formula I, formula II, and formula III.

A preferred embodiment of the present invention includes a method for treating a phosphatidylinositol 3-kinase-dependent condition in a mammal comprising administering to said mammal a phosphatidylinositol 3-kinase inhibiting amount of a compound selected from the group consisting of compounds of formula I, formula II, and formula III. PI 3-kinase-dependent conditions include biochemical processes relevant to pain, diabetes, inflammation, platelet aggregation, vascular diseases such as atherosclerosis, restenosis, and the like, and, particularly, abnormal cell growth as found in neoplasms.

Thus, an especially preferred embodiment of the present invention includes a method of treating phosphatidylinositol 3-kinase-dependent neoplasms, particularly various lymphosarcomas, with a compound selected from the group consisting of compounds of formulae I, II, and III. Other PI 3-kinase-dependent neoplasms include, for example, adenocarcinoma of the female breast, colon cancer, epidermid cancers of the head and neck, leukemia, melanoma, ovarian carcinoma, plasma cell myeloma, and squamous or small-cell lung cancer. For the treatment of these and other neoplastic PI 3-kinase-dependent conditions, the use of wortmannin is preferred.

For therapeutic treatment of the specified indications, a compound of formula I, II or III may be administered as such, or can be compounded and formulated into pharmaceutical compositions in unit dosage form for parenteral, transdermal, rectal, nasal or intravenous administration or, preferably, oral administration. Such pharmaceutical compositions are prepared in a manner well known in the art and comprise at least one active compound selected from the group consisting of compounds of formulae I, II, and III associated with a pharmaceutically carrier. The term "active compound", as used throughout this specification, refers to at least one compound selected from compounds of formula I, II, and III, or pharmaceutically acceptable salts thereof.

In such a composition, the active compound is known as "active ingredients". In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium sailcate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient. The term "unit dosage form" refers to physically discreet units suitable as unitary dosages for human subjects and other mammals, each unit containing a predetermined quantity of active material calculated to produce the desired therapeutic effect, in association with the required pharmaceutically acceptable carrier. By "pharmaceutically acceptable", it is meant the carrier, diluent or excipient must be compatible with the other ingredients of the formulation and not deleterious to the recipient thereof.

The following formulation examples are illustrative only and are not intended to limit the scope of the invention in any way. The meaning of the term "active ingredient" is as defined above.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
|---|---|
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S.

sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient(s) | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 mL |

Compounds of formulae I, II, and III are effective against PI 3-kinase and PI 3-kinase-dependent conditions over a wide dosage range. For example, daily dosages will normally fall within the range of about 0. mg/kg to about 50 mg/kg of body weight. In the treatment of adult humans, the dosage range from about 5 mg/kg to about 25 mg/kg, in single or divided doses, is preferred. However, it will be understood that the amount of the compound actually administered will be determined by a physician in light of the relevant circumstances including the relative severity of a disease state, the choice of compound to be administered, the age, weight, and response of the individual patient, and the chosen route of administration. Therefore, the above dosage ranges are not intended to limit the scope of this invention in any way.

Compounds of formulae I, II, and III have demonstrated selective activity against PI 3-kinase. The following is a description of the test systems used to demonstrate this activity.

PURIFICATION OF PHOSPHATIDYLINOSITOL 3-KINASE

PI 3-kinase may be prepared by multiple methods. In one method, PI 3-kinase was prepared from confluent Swiss 3T3 cells obtained from the American Type Culture Collection, Rockville, Md. Prior to purification of PI 3-kinase, cells were maintained in bulk culture in Dulbecco's Modified Eagles Medium (DMEM; Sigma, St. Louis, Mo.) supplemented with 10% fetal calf serum and were passaged using 0.25% trypsin and 0.02% ethylenediaminetetracetic acid (EDTA). $24 \times 10^6$ cells on four, 100 mm culture plates were washed with 10 mL Hanks Balanced Salt Solution (HBSS; Sigma) pH 7.4, and the cells were left in DMEM without fetal calf serum for 1 hour before being stimulated for 15 minutes with 100 ng/mL of the recombinant human BB homodimer of platelet derived growth factor (PDGF; Genzyme, Cambridge, Mass.). The medium was aspirated and the cells washed with 10 mL of HBSS before being lysed with 3 mL of 137 mM NaCl, 20 mM of Tris (pH 8.0) containing 1 mM of $MgCl_2$, 10% of glycerol, 1% of Triton X-100 (Rohm and Haas, Philadelphia, Pa.), 2 µg/mL of leupeptin, 2 µg/mL of aprotonin, 1 µM or phenylmethylsulfonyl fluoride (PMSF), and 1 mM of sodium orthovanadate. The cells were scraped free from the surface of the dish and centrifuged at $6,000 \times$ g for 10 minutes. The supernatant was mixed with 50 µL of washed IgG2bk antiphosphotyrosine antibody beads (Upstate Biotechnology Inc., Lake Placid, N.Y.) in 1.5 mL tubes. The tubes were capped and rotated for 2 hours at 4° C. and the beads were twice washed with 1 mL of HBSS containing 2 µg/mL of leupeptin, 4 µg/mL of aprotonin, 1 mM of PMSF, 200 µM of adenosine, and 1 mM of sodium orthovanadate. The tyrosine phosphorylated PI 3-kinase was eluted from the beads with 200 µL/tube of 10 mM Tris (pH 7.5), 2M of NaCl, 1 mM of EDTA, 200 µM of adenosine, and 10 mM of sodium phenylphosphate.

In another, preferred, method, PI 3-kinase was prepared from bovine brain. Two bovine brains (wet weight about 900 g) were obtained from a local slaughterhouse within minutes of slaughter, packed on ice, and homogenized within one hour. Brains were trimmed of excess fat and blood vessels and then homogenized using a Tekmar Tissuemizer (Cincinnati, Ohio) at 4° C. in 20 mM of Tris(pH 8.3) containing 250 mM of sucrose, 6 mM of β-mercaptoethanol, 1 µg/ml of leupeptin, 1

μg/ml of pepstatin A, 0.4 mM of PMSF, and 1 mM of MgCl$_2$.

Following centrifugation for 60 minutes at 10,000×g, the DH of the supernatant (about 1200 mL) was lowered to 5.75 using dropwise addition of 1M acetic acid at 4° C. After stirring for an additional 15 minutes at 4° C., the solution was centrifuged for 60 minutes at 13,500×g. The supernatant was discarded. Pellets were resuspended in Buffer A (20 mM of Tris, pH 8.3, containing 6 mM of β-mercaptoethanol, 0.1 mM of ethylene glycol-bis(β-aminoethyl ether) N,N,N',N'-tetraacetic acid (EGTA), 1 μg/mL of leupeptin, 1 μg/mL of pepstatin A, and 1 mM of MgCl$_2$), and loaded onto a Fast Flow Q Sepharose column (300 ml) at a flow rate of 5 mL/min at 4° C. After loading, the column was washed with 3 volumes of Buffer A containing 0.1M of KCl and the kinase was then eluted with a linear gradient of Buffer A/0.1M KCl to Buffer A/O.6M KCl at 3 mL/min over 7 volumes.

Fractions were assayed for PI 3-kinase activity using 10 μL of the fraction and phosphatidylinositol as substrate as described below. PI 4-kinase eluted in the breakthrough; PI 3-kinase eluted at approximately 0.3M of KCl. The PI 3-kinase pool was subjected to a 40% ammonium sulfate precipitation. Following centrifugation (60 minutes at 13,500×g), pellets were resuspended in Buffer B (10 mM of potassium phosphate, pH 7.4, containing 6 mM of β-mercaptoethanol, 1 μg/mL of leupeptin, 1 μg/mL of pepstatin A, and 1 mM of MgCl$_2$), and loaded onto a 50 mL hydroxylapatite column (Calbiochem, Inc., La Jolla, Calif.) at 2.5 mL/minute. The column was washed with 150 mL Buffer B until the A$_{280}$ baseline reached zero, and the kinase was then eluted with a linear gradient of 10–320 mM of KH$_2$PO$_4$ at 1 mL/minute over 450 minutes.

Active fractions were pooled and then loaded at 3 mL/minute onto a MonoS column (8 ml) (Pharmacia, Inc., Piscataway, N.J.) equilibrated in Buffer C (50 mM of MES, pH 6.2, containing 6 mM of β-mercaptoethanol, 0.1 mM of EGTA, 1 μg/mL of leupeptin, 1 μg/mL of pepstatin A, and 1 mM of MgCl$_2$). PI 3-kinase was eluted with a linear gradient of 0–0.4M KCl in Buffer C over 120 minutes. In assaying fractions, two pools of PI 3-kinase activity were routinely found. The bulk of the activity was found in the flowthrough, while about 20% of the activity was eluted in the gradient. Although the material in the gradient had considerable PI 4-kinase activity, essentially no PI 4-kinase activity was associated with the PI 3-kinase eluted in the flowthrough. Therefore, the MonoS flow-through was concentrated by tangential flow filtration on a Mini-Ultrasette Omega 50 K membrane (Filtron, Inc., Northborough, Mass.) and diluted in Buffer C to lower the conductivity. The material was then reloaded onto the MonoS column using the above conditions. The PI 3-kinase bound to the column during the wash and was ehted in the gradient. Two pools of phosphatidylinositol kinase activity were obtained in the gradient; each was assayed for PI 3-kinase and PI 4-kinase activity. Pool I was found to contain 95% PI 3-kinase activity (and 5% PI 4-kinase) while Pool II contained predominantly PI 4-kinase activity.

Pool I from the MonoS column was diluted with Buffer A and chromatographed on MonoQ (1 ml) and ehted with a gradient of 0–0.4M KCl in Buffer A. The final pool was assayed for PI 3-kinase and PI 4-kinase activity. The final product was found to contain greater than 99% PI 3-kinase activity.

ASSAY OF PURIFIED PI-3 KINASE ACTIVITY

PI 3-kinase activity was measured as previously described by Matter, W. F., et al., *Biochemical and Biophysical Research Communications*, 186:624–631 (1992). Inhibitor candidates were initially dissolved in DMSO and then diluted 10-fold with 50 mM of HEPES buffer, pH 7.5, containing 15 mM of MgCl$_2$ and 1 mM of EGTA. Ten microliters of this solution were incubated with purified bovine brain PI 3-kinase (9 μL) and phosphatidylinositol (5 μL of a 2 mg/mL stock solution in 50 mM of HEPES buffer, pH 7.5, containing 1 mM of EGTA). The final reaction mixture contained 0.1–5 ng/mL of inhibitor and 3% of DMSO (v:v). This concentration of DMSO had no effect on PI 3-kinase activity; control reaction mixtures contained 3% of DMSO (v:v) without inhibitor. Reactants were preincubated 10 minutes at ambient temperature and then the enzyme reaction was started upon addition of 1 μL [γ-$^{32}$P]ATP (2 mCi/mL, 500 μM of stock solution; 0.08 mCi/mL, 20 μM of final concentration; Dupont New England Nuclear, Boston, Mass.). The reaction was allowed to proceed for 10 minutes at ambient temperature with frequent mixing, after which time the reaction was quenched by addition of 40 μL of 1N HCl. Lipids were extracted with addition of 80 μL CHCl$_3$:MeOH (1:1, v:v). The samples were mixed and centrifuged, and the lower organic phase was applied to a silica gel TLC plate (EM Science, Gibbstown, N.J.), which was developed in CHCl$_3$:MeOH:H$_2$O:NH$_4$OH (45:35:8.5:1.5, v:v). Plates were dried, and the kinase reaction visualized by autoradiography. The phosphatidylinositol 3-monophosphate region was scraped from the plate and quantitated using liquid scintillation spectroscopy with ReadyProtein (Beckman Instruments, Inc., Fullerton, Calif.) used as the scintillation cocktail. The level of inhibition for wortmannin and analogs was determined as the percentage of [$^{32}$P]-counts per minute compared to controls.

Alternatively, products of the PI 3-kinase reaction were confirmed by HPLC as discussed by Whitman, M., *Nature*, 332:644–646 (1988). Phospholipids were deacylated in methylamine reagent and separated using a Whatman Partisphere SAX anion exchange column as previously described by Auger, K. R., *Cell*, 57:167–175 (1989). A Radiomatic Model A-140 Flo-One/Beta on-line radioactivity detector was used to monitor the deacylated [$^{32}$P]-enzyme products; deacylated [$^3$H]PI 4-monophosphate was added as an internal standard.

The inhibitor effect of wortmannin and its analogs on bovine brain purified PI 3-kinase is shown in Table 2.

| Formula | IC$_{50}$ (ng/mL) |
| --- | --- |
| Ia | 1.8 (4.2 nM) |
| Ib | 6.2 (16.7 nM) |
| II | 20.0 (59.0 nM) |
| IIIb | 1500.0 (4.6 μM) |

In addition, wortmannin and the wortmannin analogs used in the methods of the present invention have no effect on PI 4-kinase, phospholipase C, c-src protein tyrosine kinase or protein kinase C, and have a potency up to one hundred-fold greater than the previously reported activity as an inhibitor of myosin light chain kinase [See, e.g., Nakanishi, S., et al., *J. Biol. Chem.*, 267(4):2157–2163 (1992)]. Thus, wortmannin and its analogs are potent, highly selective inhibitors of PI 3-kinase.

ASSAY OF WHOLE CELL PI 3-KINASE ACTIVITY v-sis NIH 3T3 cells (National Cancer Institute, Bethesda, Md.) were selected for measuring phosphatidylinositol-3-phosphate levels because they are known to exhibit constitutive as well as platelet derived growth factor-stimulated PI 3-kinase activity. v-sis NIH 3T3 cells in logarithnic growth in a 75 cm² culture flask were placed for two hours in DMEM without fetal calf serum. The cells were washed with phosphate-free DMEM and incubated in the same medium containing 0.1% fatty acid free bovine serum, albumin and 0.15 mCi/mL [$^{32}$P]H$_3$PO$_4$ (ICN Biomedicals, Irvine, Calif.) for 70 minutes. Inhibitor candidates were prepared using the above-stated procedure, and placed in contact with the cells for 10 minutes prior to their stimulation. The cells were stimulated with 100 ng/mL of PDGF for 10 minutes. To measure phosphatidylinositol-3-phosphates in the cells, the medium was removed and the cells washed once with phosphate buffered saline before adding 4 mL/flask of HCl:methanol (1:1 by volume). The cells were scraped from the flasks and total lipids were extracted by the method described by Folch, J., et al., *J. Biol. Chem.*, 226:497–509 (1957). Deacylated lipids were prepared using methylamine via the method described by Clark, N. G., et al., *BioChem J.*, 195: 301–306, (1981), and separated by HPLC using a 10 cm RAC II Partisil 5 SAX column (Whatman, Kent, U.K.) eluted with an NH$_4$H$_2$PO$_4$ gradient at a flow of 0.8 mL/minute as described by Auger, K. R., et al., *Methods in Inositide Research*, pp. 159–166 [Irvine, R. F., Ed., Raven Press, Ltd., New York, N.Y. (1990)]. Detection of the eluting peaks was by a radioactive flow detector (Flo-One Beta, Model A515, Radiomatic Instruments, Meriden, Conn.). The reference compounds employed were deacyl-[$^3$H]phosphatidylinositol-4,5-bisphosphate and deacyl-[$^{32}$P]phosphatidylinositol-3,4,5-trisphosphate.

Although inhibition of purified PI 3-kinase was substantially greater than with PI 3-kinase inhibition in whole cells, wortmannin at 1.3 μM provided almost complete inhibition of platelet derived growth factor stimulated phosphatidylinositol-3-phosphate formation in whole cells.

In order that the invention described herein may be more fully understood, the following examples are set forth. It should be understood, however, that these examples are only for illustrative purposes and are not to be construed as limiting the scope of this invention in any manner.

EXAMPLE 1

Fermentation of Culture A24603.1

A. Shake-Flask

The culture A24603.1, either as a lyophilized pellet or as a suspension maintained in liquid nitrogen, is used to inoculate a vegetative medium having the following composition

| Vegetative Medium | |
|---|---|
| Ingredient | Amount (g/L) |
| Glucose | 10.0 |
| Glycerol | 10.0 |

-continued

| Vegetative Medium | |
|---|---|
| Ingredient | Amount (g/L) |
| Cottonseed Flour[a] | 25.0 |

Unadjusted pH = 6.3; no adjustment
[a]PROFLO Flour (Traders Protein, Memphis, TN).

The inoculated vegetetive medium was incubated in a 250 mL wide-mouth Erlenmeyer flask at 25° C. for about 72 hours on a shaker orbiting in a two-inch (5.08 cm) circle at 250 rpm.

B. Tank Fermentation of Culture A24603.1

In order to provide a larger volume of inoculum, 10 mL of incubated shake-flask medium, prepared as described in Section A, was used to inoculate 400 mL of a second-stage vegetative medium having the same composition as described above. This second-stage medium was incubated in a 2-L wide-mouth Erlenmeyer flask at 25° C. for about 23 hours on a shaker oribiting in a two-inch (5.08 cm) circle at 250 rpm.

This second-stage medium (400 mL) was used to inoculate 115 L of sterile production medium having the following composition.

| Production Medium | |
|---|---|
| Ingredient | Amount (g/L) |
| Glucose | 25.0 |
| Corn Starch | 10.0 |
| Lexein | 10.0 |
| Enzyme-hydrolyzed casein | 4.0 |
| Blackstrap molasses | 5.0 |
| MgSO$_4$ (anhydrous) | 5.0 |
| CaCO$_3$ | 2.0 |
| Deionized H$_2$O | q.s. to 115 L |

Unadjusted pH = 6.8; no adjustment.
Antifoam agent added: SAG 471[b] (0.2 gm/L).
[a]NZ Amine A (Sheffield Chemical Co., Norwich, NY).
[b]SAG 471 (Union Carbide, Sistersville, WV).

The inoculated production medium was allowed to ferment in a 115-L stirred fermentation tank for 4–5 days at a temperature of about 25° C. A dissolved oxygen level of about 45% of air saturation was maintained, as was a low rpm (180–330) in the stirred vessel.

EXAMPLE 2

Isolation and Purification of Wortmannin

Fermentation broth from Example 1 was filtered through a ceramic filter (Membralox Systems, Illinois Water Treatment, Rockford, Ill.) to yield 175 L of filtrate containing wortmannin. The pH of the filtrate was adjusted to about 3.9 with 5N HCl. The filtrate was then ehted three times with one-half volumes of ethyl acetate to give a combined volume of 207 L which was concentrated to 6 L in vacuo.

The 6 L of ethyl acetate concentrate was further concentrated in vacuo to form a dark brown viscous oil to which 500 mL of methanol was added. The mixture was swirled until the resulting crystallization was complete, filtered, briefly washed with cold methanol and dried in vacuo to give 20.4 g of wortmannin.

The methanol supernatant was reconcentrated in vacuo to form a viscous oil, dissolved in 180 mL of chloroform and applied to a 12×20 cm column of Woelm Grade 62 silica in chloroform. 5.0 L of chloroform wash was concentrated in vacuo to form a brown oil which was then dissolved in 250 mL of warm methanol. The resulting crystals were collected after 18 hours, via filtration, giving 4.2 g of wortmannin. The crystallization procedure was repeated on the remaining supernatant, yielding an additional 1.9 g of wortmannin. The identity of wortmannin was confirmed by HPLC.

We claim:

1. A method for treating a phosphatidylinositol 3-kinase-dependent neoplasm in a mammal in need of such treatment comprising administering to said mammal a phosphatidylinositol 3-kinase inhibiting amount of a compound selected from the group consisting of

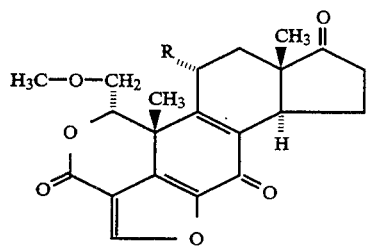

wherein R is H or acetoxy;

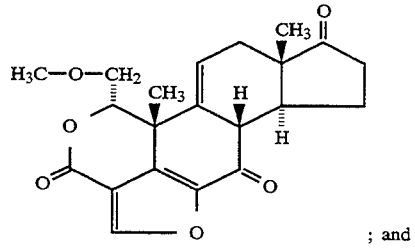

; and

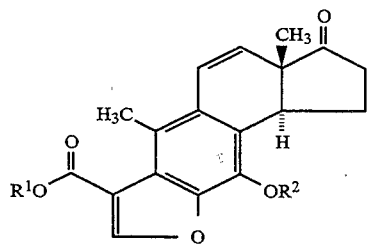

wherein
R[1] is H, methyl, or ethyl; and
R[2] is H or CH₃.

2. The method of claim 1 wherein said mammal is a human.

3. The method of claim 2 wherein said compound is a compound of formula I

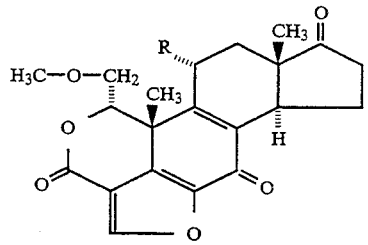

wherein R is H or acetoxy.

4. The method of claim 3 wherein R is H.
5. The method of claim 3 wherein R is acetoxy.
6. The method of claim 2 wherein said compound is a compound of formula II

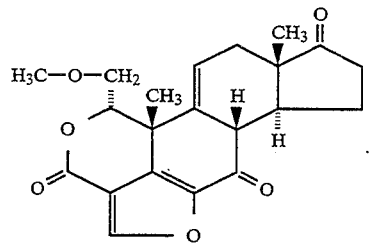

7. The method of claim 2 wherein said compound is a compound of formula III

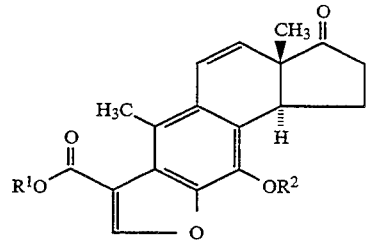

wherein
R[1] is H, methyl, or ethyl; and
R[2] is H or CH₃.

8. The method of claim 7 wherein R[1] is H and R[2] is H.
9. The method of claim 7 wherein R[1] is methyl and R[2] is H.

* * * * *